US006528682B1

(12) United States Patent
Bosch Lladó et al.

(10) Patent No.: US 6,528,682 B1
(45) Date of Patent: Mar. 4, 2003

(54) PROCESS FOR PRODUCING GABAPENTIN OR PHARMACEUTICAL GRADE

(75) Inventors: Jordi Bosch Lladó, Girona (ES); Ma del Carmen Onrubia Miguel, Barcelona (ES); Eugènia Pagans Lista, Celrà (ES)

(73) Assignee: Medichem, S.A., Barcelona (ES)

( * ) Notice: Subject to any disclaimer, the term of this patent is extended or adjusted under 35 U.S.C. 154(b) by 0 days.

(21) Appl. No.: 09/959,183
(22) PCT Filed: Apr. 4, 2000
(86) PCT No.: PCT/ES00/00121
§ 371 (c)(1),
(2), (4) Date: Oct. 18, 2001
(87) PCT Pub. No.: WO00/64857
PCT Pub. Date: Nov. 2, 2000

(30) Foreign Application Priority Data

Apr. 26, 1999 (ES) .............................................. 9900858

(51) Int. Cl.[7] ..................... C07C 229/00; A61K 31/195
(52) U.S. Cl. ........................................ 562/507; 514/561
(58) Field of Search ........................... 562/507; 514/561

(56) References Cited

U.S. PATENT DOCUMENTS 4,894,476 A * 1/1990 Butler et al.

FOREIGN PATENT DOCUMENTS

WO      WO 98/28255 A1 *  7/1998

* cited by examiner

*Primary Examiner*—Johann Richter
*Assistant Examiner*—Paul A. Zucker
(74) *Attorney, Agent, or Firm*—Scully, Scott, Murphy & Presser

(57) ABSTRACT

The invention describes a process for the preparation of pharmaceutical grade gabapentin, consisting of neutralizing an alcoholic solution of gabapentin hydrochloride with basic ion exchange resins and thereafter directly isolating the gabapentin, without requiring either the formation or the isolation of intermediates other than the pharmaceutical grade product.

12 Claims, No Drawings

PROCESS FOR PRODUCING GABAPENTIN OR PHARMACEUTICAL GRADE

This application is a 371 of PCT/ES00/00121 filed Apr. 4, 2000.

FIELD OF THE INVENTION

The present invention relates to a process for the preparation of gabapentin suitable for pharmaceutical use by neutralization of alcoholic solutions of gabapentin hydrochloride with basic ion exchange resins.

PRIOR ART REFERENCE

Gabapentin is a synthetic amino acid related to γ-aminobutyric acid (GABA), responding to the chemical name of 1-(aminomethyl)cyclohexaneacetic acid (The Merck Index, Ed. XII) and the following formula

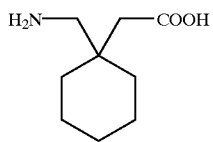

The said compound has a therapeutical activity for convulsive type cerebral disorders, such as epilepsy, hypokinesia, including fainting, and other brain trauma and, in general, it is deemed to produce an improvement of the cerebral functions.

Gabapentin and several processes for the preparation thereof are described in Spanish patent ES-A-443 723, corresponding to U.S. Pat. No. 4,024,175, Example 1 of which describes the preparation of the free amino acid from the hydrochloride thereof, by treatment of an aqueous solution thereof with a basic ion exchanger, evaporation of the solvent and subsequent crystallization from a mixture of ethanol/ether. This process, which is only outlined without details in the said patents, has drawbacks for the industrial application thereof derived from having to evaporate large amounts of water, with the high energy consumption required thereby, and involving the use of a solvent such as ether, which is extremely dangerous and hard to handle on an industrial scale.

The product obtained with the above process corresponds to a non-hydrated crystalline form coinciding with the one shown by the commercial pharmaceutical Neurontin®, which is the pharmaceutical standard for gabapentin.

Subsequently, EP-B-0 340 677 discloses a process for preparing said non-hydrated crystalline form requiring the prior preparation of a new hydrated form of gabapentin, characterized by the X-ray diffraction data thereof. Said process consists of the following successive steps:
a) passing an aqueous gabapentin hydrochloride solution through a basic ion exchange column.
b) concentrating the eluate to form a suspension.
c) cooling and adding alcohol to the above suspension.
d) cooling and centrifuging the thus prepared suspension.
e) drying the product obtained, which is the hydrated form of gabapentin.
f) dissolving the above pure hydrated form in methanol.
g) diluting and cooling the thus prepared solution until a suspension is obtained.
h) centrifuging the suspension and drying the product, which is the non-hydrated form of gabapentin.

The above described process is obviously complicated from the industrial point of view, since it requires several steps, the evaporation of large amounts of water and the isolation of an intermediate in pure form, the hydrated form, prior to a final crystallization. All of this means that the process is complex, there is an excessive occupation of the industrial plant and losses in the yield of the desired product.

It is disclosed in U.S. Pat. No. 5,319,135, col. 13, lines 47 et seq. that the products to which it relates, among which there is gabapentin, may be prepared from the acid addition salts thereof, e.g., from the hydrochlorides, by their neutralization with a long list of bases, among which there are the free amines and basic ion exchange resins. However, the examples of said patent only describe the use of the said resins for neutralizing aqueous solutions, i.e., a method coinciding with the one already described in the aforementioned patents ES-A-443 723 and EP-A-0 340 677. Example 6 of U.S. Pat. No. 5,068,413 also describes a process coinciding essentially with the one described in the above patents.

Patent application WO-A-98/28255 discloses a method for preparing gabapentin base consisting of dissolving gabapentin hydrochloride in a solvent and neutralizing it by addition of an amine in solution, said solvent being chosen in such a way that the amine hydrochloride formed during the neutralization is more soluble therein than the anhydrous gabapentin. In accordance with the above patent application, a new form of anhydrous gabapentin, named form III, is prepared in the neutralization process. It is necessary to reprocess this form III by digestion or recrystallisation in another solvent, to be able to prepare the pharmaceutical grade anhydrous gabapentin base, which is named form II in the said patent application.

This process does not require the use of ion exchange resins, but has the drawback that, unless closely adjusted amounts of neutralizing amine are used, the product obtained may be contaminated with appreciable amounts of the amine used in the neutralization and which have to be removed subsequently from the end product, by additional purification steps. Therefore, it is proposed in Example 1 of the patent application, which lays down the guidelines for the rest of the preparative Examples described therein, to use an evident molar deficit of amine relative to the gabapentin hydrochloride, which has indubitable repercussions in the form of a reduction of the yield of the product obtained. Furthermore, this process also requires the preparation of an intermediate, the so-called form III, which has to be reprocessed, with the consequent complication of the operative process.

There is, therefore, a need for developing alternative processes for the preparation of pharmaceutical grade gabapentin, allowing the industrial preparation of this product to be simplified and, therewith, the production costs to be reduced.

OBJECT OF THE INVENTION

It is the object of the invention to provide a simplified process for the preparation of pharmaceutical grade gabapentin, not requiring the preparation of intermediates which have to be reprocessed.

DESCRIPTION OF THE INVENTION

The process according to the present invention consists, in the essential aspects thereof, of:
(i) dissolving gabapentin hydrochloride in a short chain alcohol, (ii) treating the solution obtained with a basic ion exchange resin, (iii) concentrating the resulting solution until a dense anhydrous gabapentin suspension is formed in the rest of the alcoholic solvent, (iv) adding to the suspension formed in the previous step a mixture of a short chain alcohol and water and heating until the precipitate is completely redissolved, and (v) precipitating the anhydrous gabapentin by cooling and recovering the product obtained by filtering and drying.

Both the gabapentin precipitated during the concentration step (iii) and that obtained as end product are anhydrous gabapentin base with the crystalline structure proper to the conventional pharmaceutical grade product, as is to be gathered from the substantial coincidence of the IR spectrum and the X-ray powder diffractogram thereof with those of the said conventional product.

The starting gabapentin hydrochloride may be prepared by the processes described in any of patents ES-A-443 723 and EP-B-0 340 677, although other additional descriptions may be cited, such as those contained in patents U.S. Pat. No. 5,132,451, U.S. Pat. No. 5,319,135, U.S. Pat. No. 5,362,883, U.S. Pat. No. 5,068,413, U.S. Pat. No. 5,091,567, U.S. Pat. No. 5,095,148, U.S. Pat. No. 5,130,455, U.S. Pat. No. 5,136,091 and U.S. Pat. No. 5,149,870. The said starting hydrochloride may be used in anhydrous form or be hydrated with variable proportions of water ranging from 2% to 12% by weight and does not require prior purification, whereby the crude gabapentin hydrochloride obtained from the previous synthesis steps may be advantageously used as starting product.

Both the short chain alcohol of step (i) and that of step (iv) of the process according to the invention are selected from among the straight or branched chain $C_1$–$C_4$ aliphatic alcohols, such as methanol, ethanol, n-propanol, isopropanol, etc, although the use of methanol is preferred in both cases.

The basic ion exchange resins are selected from among those regularly available in commerce, well known to the man of the art, such as for example the commercial products BAYER MP-62 or AMBERLITE® IRA-67.

The alcoholic gabapentin hydrochloride solution is preferably made to interact with the resin by passing the said solution through a column filled with a sufficient amount of resin for the ion exchange capacity thereof to be above the stoichiometric level required for a complete neutralization, ranging preferably from 1.1 to 3 exchange resin equivalents for each gabapentin hydrochloride equivalent, more preferably from 1.5 to 2.5 equivalents.

The alcoholic gabapentin base solution obtained after neutralization with the ion exchange resins is concentrated by distillation of the solvent at reduced pressure, in such a way that the temperature does not exceed 50° C., preferably 35° C., and said concentration is continued until a dense suspension is formed.

The anhydrous gabapentin suspension obtained from the concentration step is redissolved using a mixture of a short chain alcohol and water, with a alcohol/water ratio ranging from 60:40 to 90:10 (v/v), preferably ranging from 70:30 to 85:15 (v/v), and heating the mixture to a temperature not higher than the reflux temperature of the solvent mixture, preferably ranging from 55° C. to 75° C.

The solution obtained is allowed to cool, it being desirable, although not strictly necessary, to seed it with some crystals of pharmaceutical grade anhydrous gabapentin when the temperature of the said solution lies between 30° C. and 50° C. In order to complete the precipitation exhaustively, it is preferable to add, when the suspension is at room temperature, an alcoholic solvent of lower gabapentin-dissolving capacity, for example isopropanol. Subsequently, cooling is continued to a temperature below 5° C. The suspension formed is held at this temperature for an additional period of time. The product is filtered and dried by conventional means, well known to the man of the art.

As stated above, both the gabapentin precipitated during the concentration step and the gabapentin crystallized as end product are anhydrous gabapentin base having the conventional crystalline structure of the pharmaceutical grade product, which clearly shows that the process according to the invention does not require either the formation or the isolation of intermediates other than the pharmaceutical grade product.

The process according to the invention is simple and economical, since it only requires simple industrial operations, the yields obtained are good and the consumption of raw materials is very adequate, since the resins used may be regenerated with very good results and all the solvents used may be recovered.

The following Examples are given to provide the man of the art with a sufficiently clear and complete explanation of the present invention, but must not be considered to be limitations of the essential aspects of the object of the invention, as have been expressed in the foregoing paragraphs of this description.

EXAMPLES

Example 1

48 g of crude gabapentin hydrochloride, equivalent to 42.5 g of product, were dissolved in 880 mL of methanol and the resulting solution, after being filtered to remove insoluble impurities, was fed through a column filled with 280 mL of weakly basic ion exchange resin BAYER MP-2, having an ion exchange capacity of 1.5 meq/mL, which had been previously washed with water, under counterflow and afterwards with methanol to remove the water. The flow-rate of the methanolic solution was 28 mL/min and, after the solution had passed completely, a methanol flow was continued until the gabapentin content in the eluate, determined by comparison with a thin layer chromatographic standard, was below 0.1%. In all, 1200 g of methanolic solution were obtained, with a gabapentin base content of 32.5 g (Yield= 93%).

The methanolic solution obtained was concentrated by low pressure distillation, such that the internal temperature did not rise above 30° C., until a dense suspension was formed in the distillation vessel, having an approximate volume of 30 mL. An aliquot sample was filtered and showed an IR spectrum (KBr) and an X-ray powder diffractogram essentially coincident with those obtained from a standard pharmaceutical grade anhydrous gabapentin sample.

To the dense suspension obtained, there was added a mixture containing 81 mL of methanol and 21 mL of water. The mixture was heated to 65° C., causing redissolution of the precipitate. Thereafter, it was allowed to cool to 40° C., was seeded with some crystals of pharmaceutical grade anhydrous gabapentin and cooling was continued down to 20° C., at which temperature 82 mL of isopropanol were added over a period of ten minutes. The suspension formed was cooled down to a temperature ranging from 0° C. to 5° C. and was held at that temperature for a further two hours. After filtering and drying under vacuum, at a temperature below 40° C., 23.4 g of pharmaceutical grade anhydrous gabapentin were obtained (Total yield relative to gabapentin hydrochloride=66.5%).

Example 2

Operating in the same way as in Example 1, but using for the same amounts 250 mL of weakly basic ion exchange resin AMBERLITE° IRA-67, having an ion exchange capacity of 1.6 meq/mL, 23.2 g of pharmaceutical grade anhydrous gabapentin were obtained (Total yield relative to gabapentin hydrochloride=66.0%).

What is claimed is:

1. A process for the preparation of pharmaceutical grade gabapentin, comprising the steps of:
   (i) dissolving gabapentin hydrochloride in a short chain alcohol,
   (ii) treating the solution obtained in step (i) with a basic ion exhange resin,
   (iii) concentrating the solution obtained in step (ii) until a dense anhydrous gabapentin suspension is formed,
   (iv) adding to the suspension formed in step (iii), a mixture of a short chain alcohol and water and heating until the precipitate is completely redissolved, and
   (v) precipitating the anhydrous gabapentin by cooling and recovering product by filtering and drying.

2. The process of claim 1, characterized in that the short chain alcohol of steps (i) and (iv) is selected from among the straight or branched chain $C_1$–$C_4$ aliphatic alcohols.

3. The process of claim 2, characterized in that the short chain alcohol of steps (i) and (iv) is methanol.

4. The process of claim 1, characterized in that the alcoholic gabapentin hydrochloride solution is made to interact with the resin by passing the said solution through a column filled with a sufficient amount of resin for the ion exchange capacity thereof to be above the stoichiometric level required for a complete neutralization.

5. The process of claim 4, characterized in that from 1.1 to 3 ion exchange resin equivalents are used for each gabapentin hydrochloride equivalent.

6. The process of claim 5, characterized in that from 1.5 to 2.5 ion exchange resin equivalents are used for each gabapentin hydrochloride equivalent.

7. The process of claim 1, characterized in that the alcoholic solution is concentrated in step (iii) at a temperature below 50° C.

8. The process of claim 1, characterized in that the mixture of a short chain alcohol and water of step (iv) has an alcohol/water ratio ranging from 60:40 to 90:10 (v/v).

9. The process of claim 8, characterized in that the mixture of a short chain alcohol and water of step (iv) has an alcohol/water ratio ranging from 70:30 to 85:15 (v/v).

10. The process of claims 1, 8 or 9, characterized in that in step (iv), the dense suspension obtained from the previous step is redissolved at a temperature ranging from 55° C. to 75° C.

11. The process of claim 1, characterized in that the precipitation of step (v) is aided by seeding with pharmaceutical grade anhydrous gabapentin crystals.

12. The process of claim 1, characterized in that isopropanol is added during the cooling of step (v).

* * * * *